US012577181B2

(12) United States Patent
Baker et al.

(10) Patent No.: US 12,577,181 B2
(45) Date of Patent: Mar. 17, 2026

(54) METHOD FOR SHUTTING DOWN A FISCHER-TROPSCH REACTOR

(71) Applicant: JOHNSON MATTHEY DAVY TECHNOLOGIES LIMITED, London (GB)

(72) Inventors: Robert Miles Baker, London (GB); Jay Simon Clarkson, Stockton-on-Tees (GB); Andrew James Coe, London (GB); Robert William Gallen, Reading (GB); Richard Philip David Pearson, London (GB); Colin Tamsett, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 461 days.

(21) Appl. No.: 18/246,254

(22) PCT Filed: Nov. 12, 2021

(86) PCT No.: PCT/GB2021/052926
§ 371 (c)(1),
(2) Date: Mar. 22, 2023

(87) PCT Pub. No.: WO2022/117984
PCT Pub. Date: Jun. 9, 2022

(65) Prior Publication Data
US 2023/0357101 A1     Nov. 9, 2023

(30) Foreign Application Priority Data
Dec. 3, 2020     (GB) ...................................... 2019079

(51) Int. Cl.
*C07C 1/04*          (2006.01)
*B01J 8/02*          (2006.01)
(Continued)

(52) U.S. Cl.
CPC ............. *C07C 1/048* (2013.01); *B01J 8/0278* (2013.01); *B01J 8/0285* (2013.01);
(Continued)

(58) Field of Classification Search
CPC ......... C07C 1/048; C07C 1/042; C07C 1/043; C07C 1/044; C07C 1/046; C07C 1/047;
(Continued)

(56) References Cited

U.S. PATENT DOCUMENTS

| | | | |
|---|---|---|---|
| 10,329,492 | B1 | 6/2019 | Agee |
| 2005/0049318 | A1 | 3/2005 | Minkkinen et al. |
| 2008/0262112 | A1 | 10/2008 | Marion et al. |

FOREIGN PATENT DOCUMENTS

| | | |
|---|---|---|
| CN | 102161609 B | 6/2013 |
| GB | 2223237 A | 4/1990 |

(Continued)

OTHER PUBLICATIONS

Cn 102161609B, machine translation, Aug. 24, 2011.*

*Primary Examiner* — Jafar F Parsa
(74) *Attorney, Agent, or Firm* — BakerHostetler

(57)     ABSTRACT

A method is described for shutting down a Fischer-Tropsch reactor fed with a reactant gas mixture comprising a synthesis gas and a recycle gas recovered from the Fischer-Tropsch reactor in a synthesis loop, said Fischer-Tropsch reactor containing a Fischer-Tropsch catalyst cooled indirectly by a coolant under pressure, comprising the steps of: (a) depressurising the coolant to cool the reactant gas mixture to quench Fischer-Tropsch reactions taking place in the Fischer-Tropsch reactor, (b) stopping the synthesis gas feed to the Fischer-Tropsch reactor, and (c) maintaining circulation of the recycle gas through the Fischer-Tropsch reactor during steps (a) and (b) to remove heat from the Fischer-Tropsch reactor. The method safely facilitates a (Continued)

more rapid return to operating conditions than a full shut-down.

21 Claims, 1 Drawing Sheet

(51) Int. Cl.
    *B01J 19/00*     (2006.01)
    *B01J 19/24*     (2006.01)
(52) U.S. Cl.
    CPC ....... *B01J 19/0013* (2013.01); *B01J 19/2465*
    (2013.01); *C07C 1/042* (2013.01); *C07C 1/043*
    (2013.01); *C07C 1/044* (2013.01); *C07C 1/046*
    (2013.01); *C07C 1/047* (2013.01); *B01J*
    *2208/00132* (2013.01); *B01J 2208/00637*
    (2013.01); *B01J 2219/00081* (2013.01); *B01J*
    *2219/00225* (2013.01); *B01J 2219/00231*
    (2013.01); *B01J 2219/00238* (2013.01); *C07C*
    *2523/745* (2013.01); *C07C 2523/75* (2013.01)
(58) Field of Classification Search
    CPC ...... B01J 2208/00637; B01J 2219/0081; B01J
    8/0285; B01J 19/0013; B01J 2219/00225
    See application file for complete search history.

(56)         References Cited

FOREIGN PATENT DOCUMENTS

| | | |
|---|---|---|
| JP | 2003292972 A | 10/2003 |
| WO | 2010/063850 A1 | 6/2010 |
| WO | 2011/048361 A1 | 4/2011 |
| WO | 2012/136971 A1 | 10/2012 |
| WO | 2016/050520 A1 | 4/2016 |

* cited by examiner

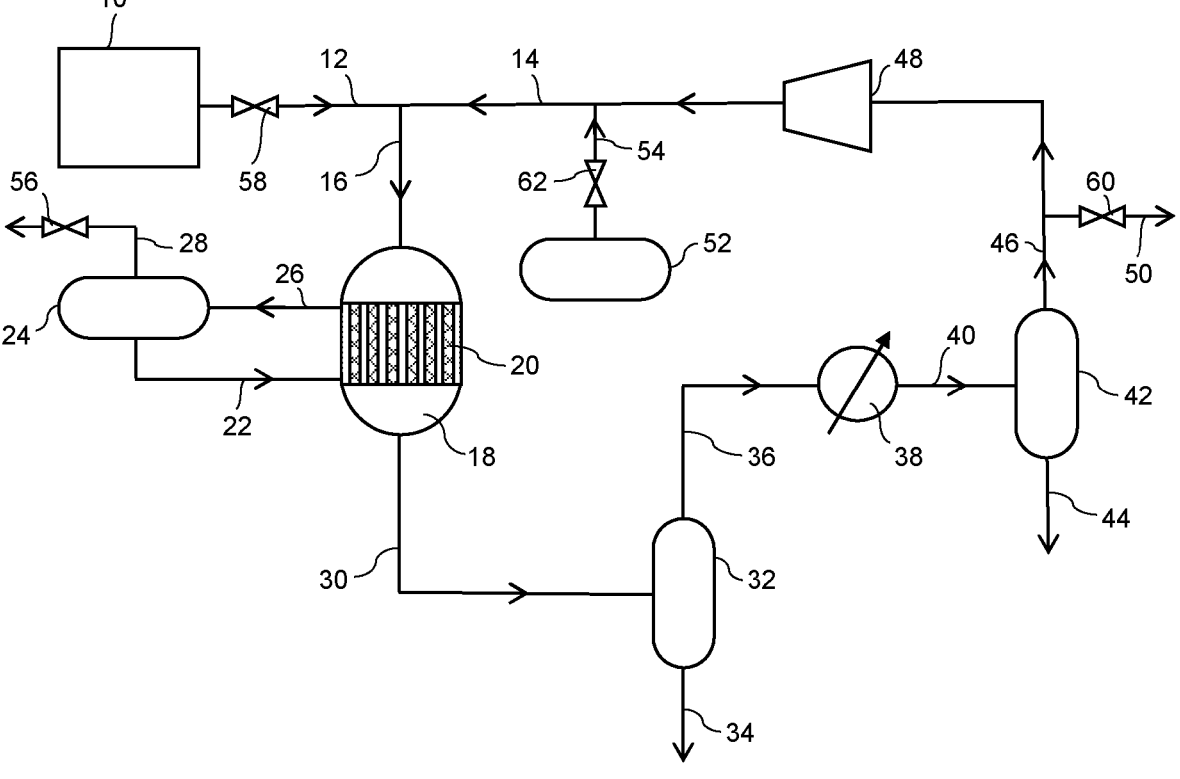

METHOD FOR SHUTTING DOWN A FISCHER-TROPSCH REACTOR

This invention relates to a method for shutting down a Fischer-Tropsch reactor and process.

The Fischer-Tropsch process involves a series of catalysed chemical reactions that produce a variety of hydrocarbons having the formula $(C_nH_{2n+2})$ from a feed gas comprising hydrogen and carbon monoxide. The process may be operated in one or more Fischer-Tropsch reactors using iron- or cobalt-based catalysts at pressures in the range of 0.1 to 10 MPa and temperatures in the range of 170 to 350° C.

The Fischer-Tropsch reactions are exothermic and various arrangements have been developed to prevent over-heating and damage to the Fischer-Tropsch reactor and catalyst, and the consequential reduction in productivity, activity and selectivity that can occur. In one arrangement, a fixed bed of Fischer-Tropsch catalyst is cooled in heat exchange with a coolant, such as boiling water under pressure.

Shutting down of the Fischer-Tropsch reactor and process, i.e. moving from an operating condition where hydrocarbons are synthesised to a non-operating condition, in a safe and efficient manner, when called for, is necessary.

GB2223237A discloses a process for the shut-down of a reactor for the preparation of an at least partly liquid hydrocarbon produced by a catalytic reaction of a synthesis gas consisting of carbon monoxide with hydrogen at elevated temperature and pressure. The reactor is provided with cooling means and with means to recycle gas through the catalyst for temperature equalizing of the catalyst. The process comprises the steps of: (i) interrupting the feed of synthesis gas; (ii) depressurizing the reactor downstream of the catalyst and providing the reactor upstream of the catalyst with inert gas; and (iii) cooling the catalyst to ambient conditions.

U.S. Ser. No. 10/329,492 discloses a process for shutting down a Fischer Tropsch reactor, the process comprising: a) stopping a reactor fresh feed; b) opening or increasing flow to a reactor tail gas purge line to maintain adequate flow through the reactor; c) allowing pressure within the reactor to drop to a level below that of a sweep gas reservoir; d) opening a sweep gas valve to allow flow from the sweep gas reservoir to a reactor inlet; e) allowing a sweep of sweep gas through the reactor to substantially remove fresh feed gas; and f) closing the sweep gas valve and blocking the purge gas line so that flow through the reactor goes to zero.

The reactor de-pressurisation and quenching with an inert or sweep gas, while effective, does not provide flexibility and necessitates an extended start-up time, subsequently. Moreover, the shut-down process is wasteful of the synthesis gas and the inventory from the synthesis loop.

The Applicants have developed an alternative shut-down method that overcomes the problems of the prior art methods.

Accordingly the invention provides a method for shutting down a Fischer-Tropsch reactor fed with a reactant gas mixture comprising a synthesis gas and a recycle gas recovered from the Fischer-Tropsch reactor in a synthesis loop, said Fischer-Tropsch reactor containing a Fischer-Tropsch catalyst cooled indirectly by a coolant under pressure, said method comprising the steps of: (a) depressurising the coolant to cool the reactant gas mixture to quench Fischer-Tropsch reactions taking place in the Fischer-Tropsch reactor, (b) stopping the synthesis gas feed to the Fischer Tropsch reactor, and (c) maintaining circulation of the recycle gas through the Fischer-Tropsch reactor during steps (a) and (b) to remove heat from the Fischer-Tropsch reactor.

The method leaves a recycle gas circulating through the Fischer-Tropsch reactor and so may be termed a partial shut-down, in contrast to a full shut-down where reactant gases may be replaced by an inert gas, such as nitrogen.

The advantages of the partial shut-down method include:
i. Purging of reactants is minimised, because the entire loop is not purged with inert gas every time.
ii. Time to restart is minimised because full depressurisation and purging is not required to be complete, before re-pressurising with fresh feed.
iii. Costly inert gas is conserved.
iv. Catalyst protection is assured by allowing the flow of reactant gases to continue, rather than relying on an inert gas to remove reactants from the catalyst.

The method is applied to a Fischer-Tropsch reactor containing a cooled Fischer-Tropsch catalyst fed with a reactant gas mixture and operated in a loop.

The reactant gas mixture fed to the Fischer-Tropsch reactor comprises a synthesis gas, plus a recycle gas, which is recovered from the Fischer-Tropsch reactor product stream. The synthesis gas for a Fischer-Tropsch process comprises hydrogen and carbon monoxide. The recycle gas will typically contain unreacted synthesis gas, carbon dioxide and potentially light hydrocarbons.

The synthesis gas may be formed using any appropriate Fischer-Tropsch synthesis gas generation technology. For example, the synthesis gas may be formed by processes including one or more steps selected from gasification, partial oxidation and catalytic partial oxidation, applied to hydrocarbon, biomass, carbonaceous and plastic waste feeds, such as coal, biomass or municipal solid waste or equivalent containing non-biogenic carbon. The synthesis gas preferably consists essentially of hydrogen and carbon monoxide. Where the resulting synthesis gas contains carbon dioxide, a carbon dioxide removal stage will typically be required to remove carbon dioxide from the reactant gas mixture upstream of the Fischer-Tropsch reactor. Carbon dioxide removal methods are known and generally comprise absorption of the carbon dioxide from the synthesis gas using a chemical or physical wash system. Impurities or contaminants that may poison the Fischer-Tropsch catalysts are also desirably removed upstream of the Fischer-Tropsch reactor using one or more contaminant removal stages by washing (absorption), and/or by passing the reactant gas mixture gas through one or beds of a suitable adsorbent, before or after any carbon dioxide removal stage.

The Fischer-Tropsch process involves a series of chemical reactions that produce a variety of hydrocarbons, ideally having the formula $(C_nH_{2n+2})$. The more useful reactions produce alkanes from the reactant gas mixture as follows:

$$(2n+1)H_2 + nCO \rightarrow C_nH_{2n+2} + nH_2O,$$

where n is typically 5-100 or higher, with preferred products having n in the range 10-20.

The Fischer-Tropsch reactor is operated in a synthesis loop, i.e. the reactant gas mixture is fed to the Fischer-Tropsch reactor where it reacts over the Fischer-Tropsch catalyst to form a product mixture comprising liquid and gaseous hydrocarbons, steam and unreacted gases.

The product gas mixture is cooled after leaving the Fischer-Tropsch reactor to condense steam and facilitate recovery of the liquid hydrocarbons. A portion of the unreacted gas, optionally after separation of light hydrocarbons, is returned to the Fischer-Tropsch reactor as the recycle gas thereby forming a synthesis loop. The recycle gas is combined with the synthesis gas to form the reactant gas mixture outside of the Fischer-Tropsch reactor, which allows for more efficient temperature control of the feed to Fischer-Tropsch reactor. Operating the Fischer-Tropsch reactor in a loop enhances the conversion efficiency of the process. To prevent a build-up of inert gases, a purge may be taken from the loop as a Fischer-Tropsch tail gas, which may be subjected to further processing.

The synthesis gas fed to the Fischer-Tropsch reactor may have a hydrogen to carbon monoxide molar ratio in the range 1.6:1 to 2.5:1, preferably 2.0:1 to 2.2:1.

The Fischer-Tropsch reactor may be operated, prior to shut-down, at pressures in the range 10 to 100 bar abs (0.1 to 10 MPa) and temperatures in the range 170 to 350° C. Operation over cobalt catalysts may be at 20-50 bar abs and 200-320° C. The gas-hourly-space velocity (GHSV) for continuous operation may be in the range 1000 to 25000 $hr^{-1}$.

The Fischer-Tropsch reactor contains a Fischer-Tropsch catalyst cooled indirectly by a coolant under pressure. The Fischer-Tropsch reactor may be any reactor suitable for containing a catalyst cooled indirectly by a coolant under pressure. Indirect cooling in the Fischer-Tropsch reactor may be by indirect heat exchange with the coolant and the Fischer-Tropsch reactor is conveniently a heat-exchange reactor. The Fischer-Tropsch process is normally operated at elevated pressure and accordingly Fischer-Tropsch reactor is typically a pressure vessel, such as a cylindrical vessel with domed ends. The flow through the catalyst may be axial and/or radial. The Fischer-Tropsch catalyst may be provided as a bed though which coolant-bearing tubes or plates are placed, or the catalyst may be provided in a plurality of reactor tubes that are bathed in coolant flowing around their outsides. The latter reactor technology is preferred.

Any Fischer-Tropsch catalyst may be used, but iron and cobalt Fischer-Tropsch catalysts are preferred. Cobalt-based Fischer-Tropsch catalysts are preferred over iron-based catalysts due to their lower carbon dioxide selectivity. Any cobalt Fischer-Tropsch catalysts may be used, but preferred catalysts comprise 9 to 25% wt Co supported on a suitable support material. Suitable catalysts therefore include agglomerates, pellets or extrudates comprising metal oxides such as alumina, zinc oxide, titania or silica, or mixtures thereof, on which the catalytically active metal is deposited.

In a particularly preferred arrangement, the Fischer-Tropsch catalyst is used in combination with a catalyst carrier suitable for use in a tubular Fischer-Tropsch reactor where the catalyst carrier containing the catalyst is disposed within one or more tubes that are cooled by circulating coolant, such as water under pressure. By "catalyst carrier" we mean a catalyst container, for example in the form of a cup or can, configured to allow a gas and/or liquid to flow into and out of the carrier and through a bed of the catalyst or catalyst precursor disposed within the carrier. Any suitable catalyst carrier may be used. In one arrangement, the catalyst carrier is that described in WO2011/048361, the contents of which are incorporated herein by reference. In an alternative arrangement, the catalyst carrier may include a catalyst monolith as disclosed in WO2012/136971, the contents of which are also incorporated herein by reference. In yet another alternative arrangement, the catalyst carrier may be that disclosed in WO2016/050520, the contents of which are also incorporated herein by reference. In preferred embodiments, the Fischer-Tropsch hydrocarbon synthesis unit comprises a tubular Fischer-Tropsch reactor in which catalyst carriers containing a Fischer-Tropsch catalyst are disposed within one or more tubes cooled by a cooling medium.

The pressure of the coolant may be the same as or similar to the pressure of the reactant gas mixture fed to the Fischer-Tropsch reactor.

The coolant may be any coolant effective under pressure to remove the heat from the Fischer-Tropsch reactor but is preferably boiling water under pressure. The water may be any suitable cooling water. The heat from the Fischer-Tropsch reactor is thereby removed by creating steam, which is preferably fed to a steam drum coupled to the Fischer-Tropsch reactor.

The Fischer-Tropsch reaction above produces FT water as a by-product of the reaction. This FT water is separated in the Fischer-Tropsch hydrocarbon synthesis unit from the hydrocarbon mixture produced by the Fischer-Tropsch reaction. The separation may be performed conveniently using one or more gas-liquid or liquid-liquid separators.

The separation of the co-produced water from the product mixture produced in the Fischer-Tropsch reactor stage allows recovery of the product mixture of hydrocarbons. Gaseous hydrocarbons may be recovered for sale or recycled to the process, for example as feed to the synthesis gas generation unit as part of, or along with, the Fischer-Tropsch tail gas. Liquid hydrocarbons may be recovered for sale or subjected to upgrading to provide more valuable hydrocarbon products. The Fischer-Tropsch hydrocarbon synthesis unit therefore desirably produces one or more hydrocarbon streams, including but not limited to a molten hydrocarbon wax and/or light hydrocarbon condensate, which is liquid at ambient temperature. The hydrocarbon products synthesised in the Fischer-Tropsch hydrocarbon synthesis unit may be used directly, for example to make base oils, or may be subsequently treated to make other products.

The shut-down method comprises a step (a) of depressurising the coolant to cool the reactant gas mixture to quench Fischer-Tropsch reactions taking place in the Fischer-Tropsch reactor. The coolant and Fischer-Tropsch reactor are preferably cooled in this step to 150° C. or below, for example to a temperature in the range 100 to 150° C. by lowering the pressure of the coolant, e.g. where the coolant is boiling water, by lowering the pressure to about 5 bar abs or below. The depressurisation may be accomplished by depressurising a steam drum coupled to the Fischer-Tropsch reactor. The de-pressurisation step (a) may be conveniently provided using an orifice and/or a control valve connected to the steam drum. The depressurisation via an orifice alone or in combination with one or more control valves offers an improved level of control for the method. The depressurisation is desirably fast enough to rapidly quench the reaction and stop carbon deposition from carbon monoxide decomposition forming on the catalyst, but not so fast as to cause mechanical damage to the Fischer-Tropsch reactor and accompanying cooling apparatus. For example, too fast a depressurisation in a water-cooled system can cause liquid water to enter into vapour lines, causing steam hammer and potential equipment/piping damage. The depressurisation of the coolant may suitably occur over a period of 5 to 10 minutes depending on catalyst activity. The starting pressure, i.e. the pressure during normal operation may be in the range 15 to 35 bar abs depending on the operating temperature used to obtain optimum performance of the catalyst. The end pressure, i.e. the pressure after de-pressurisation may be 5 bar abs or less. The rate of depressurisation is preferably in the range 2 to 6 bar per minute. The rate of depressurisation will decay over time if only an orifice is used but could be constant if a valve-controlled system is used.

The shut-down method also comprises a step (b) of stopping the synthesis gas feed to the Fischer Tropsch reactor. Step (b) is preferably performed at the same time as the depressurising step (a), i.e. steps (a) and (b) are preferably performed simultaneously. A small delay between first commencing step (a) and then commencing step (b) may be permissible but because a delay between commencing step (b) first and then commencing step (a) risks carbon formation on the catalyst, step (a) is preferably the first step. Stopping the synthesis gas mixture feed reduces the amount of reaction taking place in the Fischer-Tropsch reactor. The synthesis gas stream diverted from the Fischer-Tropsch reactor may be vented or returned to the synthesis gas generation stage or used as a fuel.

The shut-down method also comprises a step (c) of maintaining circulation of the recycle gas in the loop and through the Fischer-Tropsch reactor during steps (a) and (b) to remove heat from the Fischer-Tropsch reactor. The recycle gas stream will normally be at a lower pressure than the synthesis gas and so will be circulated by means of a circulating compressor. This circulation is maintained after the synthesis gas feed to the Fischer-Tropsch reactor is stopped. Because the recycle gas contains some hydrogen and carbon monoxide, some additional Fischer-Tropsch synthesis may take place but this is limited by the cooling of the Fischer-Tropsch reactor caused by the depressurisation of the coolant. Any liquid hydrocarbons and co-produced water formed during step (c) may be recovered as normal. As a result, whereas the Fischer-Tropsch reactor and loop are not depressurised, e.g. via the purge, the loop pressure will drop slightly due to the conversion of the reactant gases into liquids until the Fischer-Tropsch reactions are quenched.

The Fischer-Tropsch reactor loop can be left circulating in this mode, safely, for as long as is required. The method allows the Fischer-Tropsch reactor and process to enter a standby condition, without having to vent (e.g. to flare) the entire inventory of the reactor system i.e. the system is held at pressure ready for restart. Even if a full reactor purge is required before restart, this is still an operational benefit, as it permits an operator to do so in a controlled manner, at a time of the operators choosing.

The method may precede a re-start of the process, or if required, a full shut-down.

Where a re-start of the process following the partial shut-down method is required, then the method may further comprise the steps of: (d1) reducing the pressure of the Fischer-Tropsch reactor and circulating recycle gas, (e1) adjusting the inert gas content of the circulating recycle gas to a minimum value, (f1) re-pressurising the Fischer-Tropsch reactor with synthesis gas feed, and (g1) re-pressurising the coolant thereby increasing the Fischer-Tropsch reactor temperature until Fischer-Tropsch reactions begin to occur, and (h1) introducing synthesis gas to the Fischer-Tropsch reactor.

In step (d1) the depressurising of the Fischer-Tropsch reactor and circulating recycle gas may conveniently be accomplished using the synthesis loop purge. The Fischer-Tropsch reactor pressure may be reduced to pressure in the range 5-10 bara, the optimal value for which will depend on the specific plant. Preferably, the pressure is below the inert gas supply, e.g. the nitrogen supply, to facilitate rapid supply of inert gas into the Fischer-Tropsch reactor and loop if needed.

In step (e1) the inert gas may comprise nitrogen, carbon dioxide, methane and other light hydrocarbons. The reactant, non-inert gases, i.e. the hydrogen and carbon monoxide, will also be present because the Fischer-Tropsch reactor and catalyst temperature has been reduced in consequence of step (a) to quench the Fischer-Tropsch reactions. The minimum inert gas content of the circulating recycle gas may be in the range of 60 to 80% by volume. The optimal value will depend on the specific plant design and the pressure that was chosen to reduce to in step (d1). If inerts are too low, the pressure can be reduced further and topped back up using an inert gas, such as nitrogen. If inerts are too high, the system pressure could be reduced further, with no subsequent top-up with inert gas. Step (e1) is required because the inert content present in the circulating gas can vary as a result of how active the catalyst was at time the shut down method was instigated and how long the Fischer-Tropsch reactor took to quench in step (a). Inerts being too high may lead to a sluggish start-up, which may lead to Fischer-Tropsch reactor temperatures being increased too rapidly, which may in turn lead to catalyst damage or even runaway. In contrast, too low a level of inerts may lead to a more hard-to-control start-up, which may cause catalyst damage from the reaction exotherm.

In step (f1) the pressure may be raised to a pressure which may be at or below the original operating pressure but is typically 60 to 100% of the operating pressure prior to the shutdown. The Fischer-Tropsch catalyst at this stage will be below the normal, pre-shut-down temperature and so there will be essentially no conversion or consumption of the synthesis gas, and so the re-pressurisation is stopped once the desired reactor pressure has been reached.

In step (g1) the re-pressurisation should be sufficient to increase the Fischer-Tropsch catalyst temperature to an operating condition, i.e. a temperature at which the Fischer-Tropsch reactions commence. Where the coolant is boiling water under pressure, this may be achieved by re-pressurising the steam drum coupled to the Fischer-Tropsch reactor using suitable means, for example a steam eductor/jet-pump loop.

In step (h1), the synthesis gas feed to the Fischer-Tropsch reactor is re-commenced. The synthesis gas feed is desirably introduced with the circulating recycle gas to provide the desired hydrogen to carbon monoxide molar ratio at the inlet of the Fischer-Tropsch reactor. The loop purge may be used to control the pressure in the Fischer-Tropsch reactor and loop. If the synthesis gas re-pressurisation in step (f1) was to below the desired operating pressure, e.g. the operating pressure prior to the partial shutdown, the pressure can be increased in step (h1) back to the desired operating pressure.

As an alternative to a re-start of the process, the Fischer-Tropsch reactor may be fully shut down from the partially shut-down state. Where a full shut-down of the process following the partial shut-down method is required, then the method may further comprise the steps of: (d2) stopping the circulation of the recycle gas, (e2) feeding the inert gas feed into the Fischer-Tropsch reactor and loop at a pressure greater than the pressure of the Fischer-Tropsch reactor and loop, and (f2) purging the Fischer-Tropsch reactor and loop of reactant gases using the inert gas feed to displace the recycle gas.

In step (d2) the circulation of the recycle gas is stopped.

In step (e2) the inert gas, e.g. nitrogen, is supplied to provide a safely inerted Fischer-Tropsch reactor system. The inert gas will displace non-inert gases (i.e. the hydrogen and carbon monoxide) away from the catalyst and prevent catalyst damage, e.g. by carbon deposition. The inert gas may conveniently be stored in a pressurised tank dedicated for this purpose, or a constant high-pressure inert gas supply may be used. The pressure of the inert gas supply, e.g. the nitrogen supply, to facilitate supply of inert gas into the Fischer-Tropsch reactor and loop may suitably be 10 to 30 bar above the Fischer-Tropsch reactor and loop pressure.

In step (f2) the purging of the Fischer-Tropsch reactor and circulating recycle gas may conveniently be accomplished using the synthesis loop purge. If the pressure of the inert gas supply decays as the recycle gas is displaced, the Fischer-Tropsch reactor pressure may be reduced via the purge device, e.g. orifice or valve, to maintain a differential pressure sufficient to displace the reactant gases and provide sufficient cooling flow to the Fischer-Tropsch reactor tubes. If a constant pressure inert gas supply is used the pressure in the Fischer-Tropsch reactor and loop need not be reduced.

Steps (d2), (e2) and (f2) may be performed simultaneously or in rapid succession. Performing (d2) as the first step may be particularly advantageous in an emergency shutdown situation.

In an alternative scenario not in accordance with the present invention, it may be envisaged that a full shut-down method may comprise the steps of: (a) depressurising the coolant to cool the reactant gas mixture to quench Fischer-Tropsch reactions taking place in the Fischer-Tropsch reactor, (b) stopping the synthesis gas feed to the Fischer Tropsch reactor, (c) stopping the circulation of the recycle gas, (d) feeding the inert gas feed into the Fischer-Tropsch reactor and loop at a pressure greater than the pressure of the Fischer-Tropsch reactor and loop, and (e) purging the Fischer-Tropsch reactor and loop of reactant gases using the inert gas feed to displace the recycle gas. Steps (a), (b), (c), (d) and (e) may be performed simultaneously or in rapid succession. This method does not have the advantages of the present invention.

The shut-down method of the invention may be employed for planned shut-downs or emergency shut-downs, for example to maintain process safety, facilitate maintenance or protect the Fischer-Tropsch catalyst. The procedure may be activated manually or operated autonomously using a conventional computerised plant control system and/or plant safety-instrumented system.

The partial shut-down may be used when the plant control systems trips in response to an unexpected or un-planned condition in the process, but where the trip is not dangerous to the Fischer-Tropsch reactor and catalyst. Full shut-down, in contrast, may be performed to protect the Fischer-Tropsch catalyst against deactivation on loss of flow, or a higher-integrity protection for the catalyst against other upsets, such as a high temperature/runaway in the Fischer-Tropsch reactor.

Upon commencement of the partial shut-down method, the plant control system and/or plant safety-instrumented system may additionally instruct upstream and/or downstream operations to shut-down or enter a safe-operating state. For example, where the coolant is boiling water under pressure that generates steam, the plant control system may activate an auxiliary steam generation unit, such as a fired heater or boiler, to provide steam to replace that lost from the steam drum. Alternatively, or in addition, the plant control system may de-activate downstream units for processing the liquid and gaseous hydrocarbons recovered from the product gas from the Fischer-Tropsch reactor, and/or for processing the Fischer-Tropsch tail gas.

The invention is further described by reference to the drawings in which:

FIG. 1 is a depiction of one embodiment of a system to which the method of the present invention may be applied.

It will be understood by those skilled in the art that the drawings are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

In FIG. 1 a synthesis gas generation unit 10 produces a purified synthesis gas mixture consisting of hydrogen and carbon monoxide at elevated temperature and pressure. The synthesis gas is fed from the synthesis gas generation unit 10 via line 12 and combined with a recycle stream in line 14 to produce a reactant gas mixture which is fed via line 16 to a Fischer-Tropsch reactor 18 containing a plurality of Fischer-Tropsch catalyst-containing reaction tubes 20. The Fischer-Tropsch catalyst may be contained within a plurality of catalyst carriers within each of the reaction tubes. The tubes 20 are cooled by boiling water under pressure provided to the reactor via line 22, supplied by a steam drum 24. Steam is recovered from the Fischer-Tropsch reactor 18 via line 26 and returned to the steam drum 24. The steam drum is fed with a stream of boiler feed water (not shown) and steam is recovered from the steam drum via line 28. Hydrocarbons are synthesis by reaction of the hydrogen and carbon monoxide over the Fischer-Tropsch catalyst. A product mixture is recovered from the Fischer-Tropsch reactor 18 via line 30 and fed to a first gas-liquid separator 32 where a liquid wax product is separated from product and unreacted gases and recovered via line 34 for optional further processing. The gaseous product and unreacted gases are fed from the first gas-liquid separator 32 via line 36 to one or more heat exchangers 38 where it is cooled to condense a mixture of co-produced water and condensable hydrocarbon products. The cooled mixture formed in the one or more heat exchangers 38 is fed via line 40 to a second gas-liquid separator 42, where the condensed water and hydrocarbons are separated and recovered via line 44 for further processing. An unreacted gas mixture comprising hydrogen, carbon monoxide and possibly carbon dioxide and/or non-condensable hydrocarbons is recovered from the second gas-liquid separator 42 via line 46 and compressed in a circulating compressor 48 to form the recycle gas stream 14. A purge line 50 is taken from the unreacted gas mixture line 46 upstream of the compressor 48.

Optionally, a pressure vessel 52 containing high-pressure nitrogen at a pressure greater than the compressed recycle gas in line 14 and synthesis gas feed in line 12 may be connected to the recycle gas in line 14 via a feed line 54 downstream of the compressor 48 for use in case of emergency. In addition, it may be advantageous to have a branch line from line 54 directly to the reactant gas feed line 16 near the inlet of the Fischer-Tropsch reactor 18 to help to purge reactants from the reactor as quickly as possible.

In order to operate the partial shut-down method, a valve 56 in the steam line 28 is opened to de-pressurise the steam drum 24 coolant fed to the Fischer-Tropsch reactor 18 via line 22. At the same time a valve 58 in the synthesis gas feed line 12 is closed to stop the flow of synthesis gas to the reaction tubes 20. The de-pressurisation of the steam drum reduces the temperature of the coolant, which has the effect of quenching the reactions taking place in the reaction tubes 20. The circulating compressor 48 is operated to maintain a flow of gas through the cooled reaction tubes 20 in the Fischer-Tropsch reactor 18.

In order to re-start the process a valve 60 on the purge line 50 may be opened. Nitrogen, e.g. from a local low-pressure nitrogen source (not shown) may be used to adjust the inert gas content of the circulating gas to a level that avoids the reaction tubes 20 in the Fischer-Tropsch reactor 18 from overheating when the synthesis gas feed is restarted. Valve 58 is then re-opened to allow pressurisation of the reaction tubes 20 in the Fischer-Tropsch reactor 18. Once the desired pressure has been reached, the valve 58 is closed. Valve 56 is then closed to allow re-pressurisation of the steam drum 24 and coolant fed to the reactor via line 22. This has the effect of bringing the Fischer-Tropsch reactor 18 and reaction tubes 20 up to a temperature where the Fischer-Tropsch reactions re-commence. Once the desired temperature has been reached, valve 58 is re-opened to feed synthesis gas via line 12 to the reaction tubes 20 in the Fischer-Tropsch reactor 18.

In the event that the system is required to be fully shut-down, for example in case of emergency, then the circulating compressor 48 is stopped and a valve 62 in the high-pressure nitrogen feed line 54 opened to admit nitrogen to the reaction tubes 20 of the Fischer-Tropsch reactor 18. Valve 60 in the purge line 50 is opened to enable the inert gas to flow through the entire system.

The invention claimed is:

1. A method for shutting down a Fischer-Tropsch reactor fed with a reactant gas mixture comprising a synthesis gas and a recycle gas recovered from the Fischer-Tropsch reactor in a synthesis loop, said Fischer-Tropsch reactor containing a Fischer-Tropsch catalyst cooled indirectly by a coolant under pressure, comprising:

(a) depressurising the coolant to cool the reactant gas mixture to quench Fischer-Tropsch reactions taking place in the Fischer-Tropsch reactor, (b) stopping the synthesis gas feed to the Fischer Tropsch reactor, and (c) maintaining circulation of the recycle gas through the Fischer-Tropsch reactor during (a) and (b) to remove heat from the Fischer-Tropsch reactor, wherein the Fischer-Tropsch reactor comprises a pressure vessel in which the Fischer-Tropsch catalyst is provided within a plurality of reactor tubes that are bathed in coolant flowing around their outsides.

2. The method according to claim 1, wherein the synthesis gas consists essentially of hydrogen and carbon monoxide with a molar ratio of hydrogen to carbon monoxide in the range of 1.6:1 to 2.5:1.

3. The method according to claim 1, wherein the Fischer-Tropsch reactor, prior to shut down is operated at a pressure in the range 10 to 100 bar abs and a temperature in the range 170 to 350° C.

4. The method according to claim 1, wherein the Fischer-Tropsch catalyst is an iron Fischer-Tropsch catalyst or a cobalt Fischer-Tropsch catalyst.

5. The method according to claim 1, wherein the Fischer-Tropsch catalyst is used in combination with a catalyst carrier suitable for use in a tubular Fischer-Tropsch reactor where the catalyst carrier containing the catalyst is disposed within one or more tubes cooled by the coolant under pressure.

6. The method according to claim 1, wherein the coolant is boiling water under pressure provided by a steam drum coupled to the Fischer-Tropsch reactor.

7. The method according to claim 6, wherein the depressuring step (a) is provided using an orifice and/or a control valve connected to the steam drum.

8. The method according to claim 1, wherein the depressuring step (a) is at a rate of 2 to 6 bar per minute.

9. The method according to claim 1, wherein a temperature in step (a) is reduced to 150° C. or less.

10. The method according to claim 1, wherein the method is followed directly by a start-up of a Fischer-Tropsch process.

11. The method according to claim 10, wherein the method further comprises: (d1) reducing the pressure of the Fischer-Tropsch reactor and circulating recycle gas, (e1) adjusting an inert gas content of the circulating recycle gas to a minimum value, (f1) re-pressurising the Fischer-Tropsch reactor with synthesis gas feed, (g1) re-pressurising the coolant thereby increasing a temperature of the Fischer-Tropsch reactor until Fischer-Tropsch reactions begin to occur, and (h1) introducing synthesis gas to the Fischer-Tropsch reactor.

12. The method according to claim 11, wherein in step (d1) the pressure of the Fischer-Tropsch reactor is reduced to pressure in the range of 5-10 bara.

13. The method according to claim 11, wherein in step (e1) a minimum inert gas content of the circulating recycle gas is in the range of 60 to 80% by volume.

14. The method according to claim 11, wherein in step (f1) the pressure is raised to a pressure 60 to 100% of an operating pressure prior to the shutdown.

15. The method according to claim 11, wherein in step (g1), where the coolant is boiling water under pressure, re-pressurisation is achieved by pre-pressurising a steam drum coupled to the Fischer-Tropsch reactor using a steam eductor/jet-pump loop.

16. The method according to claim 1, wherein the method is followed by a full shut-down of a Fischer-Tropsch process.

17. The method according to claim 16, wherein the method further comprises: (d2) stopping the circulation of the recycle gas, (e2) feeding an inert gas feed into the Fischer-Tropsch reactor and loop at a pressure greater than the pressure of the Fischer-Tropsch reactor and loop, and (f2) purging the Fischer-Tropsch reactor and loop of reactant gases using the inert gas feed to displace the recycle gas.

18. The method according to claim 17, wherein in step (e2) the inert gas feed is a nitrogen gas feed.

19. The method according to claim 17, wherein in step (e2), the inert gas is supplied from a pressurised tank dedicated for the method.

20. The method according to claim 1, wherein the method is activated manually or operated autonomously using a computerised plant control system and/or plant safety-instrumented system.

21. The method according to claim 20, wherein the computerised plant control system and/or plant safety-instrumented system additionally instructs upstream and/or downstream operations to shut-down or enter a safe-operating state.

\* \* \* \* \*